(12) United States Patent
Baumann et al.

(10) Patent No.: US 12,167,836 B2
(45) Date of Patent: Dec. 17, 2024

(54) OPTICAL FILTER SYSTEM FOR A VIDEO ENDOSCOPE, DISPLAY SYSTEM AND VIDEO ENDOSCOPE

(71) Applicant: KARL STORZ SE & Co KG, Tuttlingen (DE)

(72) Inventors: Christin Baumann, Tuttlingen (DE); Harald Baumann, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 120 days.

(21) Appl. No.: 17/492,529

(22) Filed: Oct. 1, 2021

(65) Prior Publication Data

US 2022/0104693 A1 Apr. 7, 2022

(30) Foreign Application Priority Data

Oct. 2, 2020 (DE) .................... 102020125853.4

(51) Int. Cl.
*A61B 1/00* (2006.01)
*A61B 1/05* (2006.01)
(Continued)

(52) U.S. Cl.
CPC ...... *A61B 1/00186* (2013.01); *A61B 1/00096* (2013.01); *A61B 1/05* (2013.01);
(Continued)

(58) Field of Classification Search
CPC .. A61B 1/00186; A61B 1/00096; G02B 5/28; G02B 23/243; G02B 23/2484
See application file for complete search history.

(56) References Cited

U.S. PATENT DOCUMENTS

| 4,801,792 A | 1/1989 | Yamasita et al. |
| 5,296,971 A * | 3/1994 | Mori ........................ G02B 9/12 359/716 |

(Continued)

FOREIGN PATENT DOCUMENTS

| DE | 102015011429 A1 | 3/2017 |
| EP | 3251578 A1 | 12/2017 |

(Continued)

OTHER PUBLICATIONS

Obermeier, "Recherchebericht" (German Patent Office Report on Patentability), Sep. 9, 2021, pp. 1-6, DPMA, Munich.
(Continued)

*Primary Examiner* — Anh Tuan T Nguyen
*Assistant Examiner* — Shankar Raj Ghimire
(74) *Attorney, Agent, or Firm* — David N. Villalpando; Jacqueline Cohen (57) ABSTRACT

An optical filter system and a video endoscope therefor are disclosed. The optical filter system is arranged in a distal end section of a shaft. At least one image sensor for receiving image light is positioned in the distal end section. The optical filter system contains an optical filter and an objective lens system with a three or more lenses to collect image light and to pass it to the image sensor. The filter has transmission characteristics that vary relative to the radial distance from its center and is located between the first lens and the second lens of the objective lens system. Used in conjunction with fluorescence imaging, emission radiation collected by the image sensor is substantially free of excitation radiation. Additionally, a display system clearly delineating the regions with reliable fluorescence and/or visible light is also disclosed.

20 Claims, 4 Drawing Sheets

(51) Int. Cl.
    *G02B 5/28*     (2006.01)
    *G02B 23/24*     (2006.01)

(52) U.S. Cl.
    CPC ............. *G02B 5/28* (2013.01); *G02B 23/243* (2013.01); *G02B 23/2484* (2013.01)

(56) References Cited

U.S. PATENT DOCUMENTS

| | | | |
|---|---|---|---|
| 6,384,968 B1* | 5/2002 | Ito | G02B 21/06 359/385 |
| 6,476,851 B1 | 11/2002 | Nakamura | |
| 6,700,690 B1* | 3/2004 | Buchsbaum | G02B 5/20 359/578 |
| 6,796,939 B1* | 9/2004 | Hirata | A61B 1/0676 600/179 |
| 7,280,283 B1* | 10/2007 | Kasai | G02B 9/60 359/656 |
| 7,324,674 B2* | 1/2008 | Ozawa | A61B 1/043 382/128 |
| 7,511,891 B2 | 3/2009 | Messerschmidt | |
| 8,717,677 B2* | 5/2014 | Chang | G02B 5/285 359/586 |
| 8,861,106 B2* | 10/2014 | Moore | G01J 3/10 359/590 |
| 10,145,738 B2 | 12/2018 | Nieten et al. | |
| 2001/0043330 A1* | 11/2001 | Jung | G01J 3/0216 356/73 |
| 2002/0075468 A1* | 6/2002 | Antoni | G03F 7/701 355/71 |
| 2004/0233538 A1* | 11/2004 | Suga | G02B 23/243 359/819 |
| 2005/0124858 A1* | 6/2005 | Matsuzawa | A61B 1/041 600/176 |
| 2006/0066844 A1* | 3/2006 | Moribe | G01N 21/95692 356/237.5 |
| 2007/0167841 A1* | 7/2007 | Hayashi | G01N 21/6486 600/476 |
| 2009/0177043 A1* | 7/2009 | Akiyama | A61B 5/0084 600/181 |
| 2009/0290236 A1* | 11/2009 | Wang | G02B 23/243 359/753 |
| 2010/0053312 A1* | 3/2010 | Watanabe | A61B 1/00096 348/E7.085 |
| 2010/0234739 A1* | 9/2010 | Nakaoka | A61B 5/0084 600/476 |
| 2010/0245550 A1* | 9/2010 | Ishihara | A61B 1/000095 348/E7.085 |
| 2010/0245653 A1* | 9/2010 | Bodor | G02B 23/243 348/335 |
| 2014/0078276 A1* | 3/2014 | Kaneko | A61B 1/00179 348/65 |
| 2014/0288370 A1* | 9/2014 | Jungbauer | A61B 1/00105 600/112 |
| 2015/0080654 A1* | 3/2015 | Kuhn | A61B 1/051 600/111 |
| 2015/0378144 A1* | 12/2015 | Handte | A61B 1/00131 250/208.1 |
| 2015/0381909 A1* | 12/2015 | Butte | G06T 7/0012 250/578.1 |
| 2016/0231594 A1* | 8/2016 | Ang | C23C 14/24 |
| 2017/0167980 A1* | 6/2017 | Dimitriadis | A61B 3/14 |
| 2017/0176336 A1 | 6/2017 | Dimitriadis et al. | |
| 2019/0107651 A1* | 4/2019 | Sade | G02B 3/06 |
| 2019/0110686 A1 | 4/2019 | Kato | |
| 2019/0170647 A1 | 6/2019 | Ikenaga et al. | |
| 2019/0274527 A1* | 9/2019 | Spink | G02B 23/2461 |
| 2020/0195819 A1 | 6/2020 | Saito | |
| 2022/0104693 A1* | 4/2022 | Baumann | A61B 1/05 |

FOREIGN PATENT DOCUMENTS

| | | |
|---|---|---|
| WO | 2019191497 A1 | 10/2019 |
| WO | 2020067385 A1 | 2/2020 |

OTHER PUBLICATIONS

Artikis, T., "Partial European Search Report," Mar. 2, 2022, pp. 1-10, EPO, Munich.

* cited by examiner

OPTICAL FILTER SYSTEM FOR A VIDEO ENDOSCOPE, DISPLAY SYSTEM AND VIDEO ENDOSCOPE

CROSS REFERENCE TO RELATED APPLICATIONS

This application claims priority to German Patent Application No. 102021106836.3, filed Mar. 19, 2021, and German Patent Application No. 102020125853.4, filed Oct. 2, 2020, both of which are incorporated by reference.

FIELD OF THE INVENTION

The invention concerns an optical filter system for a video endoscope, and more particularly to video endoscopes used for visible and fluorescent imaging (FI). This invention is particularly relevant to distal tip video endoscopes with short optical systems, as well as to display systems for FI image data collected by such endoscopes.

BACKGROUND OF THE INVENTION

For medical or non-medical applications, endoscopes comprise an elongate shaft configured to be introduced into an internal cavity of a human or animal body or another object for examination, such as a piping. For generating an image of an object field, an imaging optic is located in a distal (meaning distant from a user) end section of the shaft. However, the distal end section only offers limited space available for the optical system, which commonly encourages the use of a single chip as image sensor in the distal tip section of an endoscope. In endoscopes with very short optical systems in the distal end section, problems arise especially in fluorescence imaging.

In fluorescence imaging, it is necessary to filter out the excitation radiation such that only the radiation emitted by the fluorophore is collected by the image sensor. While in endoscopes with long optical systems it is possible to place an interference filter to selectively filter out the excitation radiation in a position where all main rays incident on the interference filter near the same angle, such a flexible positioning of an interference filter in a short optical system is not possible. According to the state of the art, the position of a filter edge, that is the position along the electromagnetic spectrum where the filter changes from passing to blocking (or changes from blocking to passing) wavelengths depends on the angle of incidence (AO') of incident radiation. This dependency creates a problem in endoscopes with short optical systems, as interference filters generally change their band of transmission and filter edge position as the incident angle diverges from perpendicular to the surface of the filter.

Commonly, the incident angle increases radially, symmetrically to the perpendicular on the surface of the interference filter and effects that the peak transmission and shifts the filter edge towards shorter wavelengths, especially in the peripheral region of the image. Furthermore, in case of fluorescence imaging wherein the excitation wavelength and the fluorescence emission wavelength differ only by a few nanometers, a reliable fluorescence observation is difficult, because, as the AOI departs from the perpendicular to the filter surface, a greater part of the excitation light is passing the interference filter and overlays the fluorescence emission signal. Consequently, the excitation radiation in the peripheral regions of the image is falsely interpreted and displayed as fluorescence emission radiation. This can have major consequences e.g., in recognizing a tumor in a medical application or in the detection of bacteria in industrial applications.

Accordingly, likewise known display systems for endoscopes are not adapted to handle these problems and result in an only partially useable field of view (FOV) with unsure image data display, an unreliable fluorescence display, and/or an undefined transition region.

A known multi-region filter is described, for example, in U.S. Pat. No. 4,801,792 A, wherein an endoscope comprises a two-region annular electronically controlled aperture with a light transmitting section disposed along an optical axis of the objective lens unit and a variable light transmitting section surrounding the light transmitting section being capable of changing between a light transmitting state and a light interrupting state, in order to obtain a proper depth of field and brightness. Fluorescence imaging is not considered by U.S. Pat. No. 4,801,792 A.

An optical filter and a fluorescence observation system are described in DE 10 2015 011 429 B4, wherein the optical filter system includes an illumination filter and a detection filter, which each have several blocking ranges and transmission ranges. The resulting fluorescence imaging is therefore filter specific and dependent on the incident angle of the main rays.

What is therefore needed, and what is lacking in the prior art, is an optical filter and configuration that enables the reliable detection of white light as well as fluorescence imaging (FI) in a short optical system. Further, a display system that indicates which regions of the displayed image are reliable is also desired.

BRIEF DESCRIPTION OF THE INVENTION

These shortcomings of the prior art are solved by an inventive optical filter system for a video endoscope, wherein the optical filter system is arranged in a distal end section of an elongate shaft and at least one electronic image sensor for receiving image light is arranged in an image plane in the distal end section, wherein the optical filter system comprises an objective lens system with a first lens, a second lens, a third lens and/or further lenses in order from an object side to receive the image light and to pass the image light toward the image sensor and wherein an optical filter comprising varying transmission characteristics relative to a distance from a central region of the optical filter and/or from an optical axis of the incident light to the optical filter is optically located between the first lens and the second lens of the objective lens system, so that in case of fluorescence imaging an emission radiation is collectable by the image sensor substantially free of an excitation radiation and/or fluorescence image data and/or a visible light image data are overlayable and/or displayable.

Therewith, in distal tip endoscopes with a short optical system where the main rays are not all near perpendicularly incident on the surface of the optical filter, nevertheless a distinct observation and display of the detected light by the image sensor is enabled.

Due to the varying transmission characteristics of the optical filter from a central region of the optical filter and therefore from the ideal optical axis to the peripheral region and therewith the boundary of the optical filter, a shift of the respective peak transmission and of a filter edge through the optical filter to a shorter wavelength is avoided. Thus, an emission radiation of a fluorophore is collected by the image sensor free of substantial interference by the excitation radiation.

Consequently, in a 2D video endoscope with a fluorescence optic, a 2D white light image and 2D fluorescence image, a 2D overlay display of fluorescence and visible light (white light) as well as a 2D image of alternative fluorophores in overlay modes or pure fluorescence modes are possible. Likewise, for a 3D video endoscope with two separated fluorescence optics, a 3D image of visible light, a 3D image of alternative fluorophores and a 3D overlay of fluorescence and visible light are realized.

Therefore, the fluorescence functionality of a video endoscope is enhanced and optimized by the optical filter system including the optical filter with varying transmission characteristics. Hereby, it is especially advantageous that only one electronic image sensor for the visible light and the fluorescence imaging is necessary or two image sensors in case of 3D imaging.

Furthermore, an endoscope with a short optical system in its distal end tip is provided which is useable without any additional sensors or filter changers for visible light and fluorescence imaging.

Even if the light rays are not incident optimally on the surface of the optical filter, due to the varying transmission characteristics of the optical filter trustworthy fluorescence imaging data are collected and are displayable. Overall, the optical filter system allows a miniaturized, short optical system in the distal tip of a video endoscope providing enhanced and optimally separated and/or overlaid imaging and display of visible light and fluorescence by a video endoscope.

One of the primary ideas of the invention is the special design of an optical filter with a varying transmission characteristics, changing with increasing distance from the center or central region of the optical filter and/or from an optical axis of the incident image light to the optical filter for fluorescence video endoscopy with just one image sensor or two image sensors in case of 3D imaging, wherein the video endoscope comprises a short optical system in its distal end section, so that at no position within the optical system a location of the optical filter is possible in which all main rays for the entire image area have an almost identical angle of incidence and therefore under these constraints by the optical filter located directly between the first lens and the second lens of the objective lens system nevertheless by the varying transmission characteristics from the central region of the optical filter to its peripheral area, both the influence of the incident angles on the image observation and display as well as interference of excitation radiation with emission radiation in fluorescence imaging are compensable.

Therewith, by the optical filter system, the optical filter is insertable at a position where the main rays have a disadvantageous incident angle and incident direction and wherein the incident angles increase towards the peripheral region and to rim of the optical filter.

As utilized in accordance with the present disclosure, the following terms, unless otherwise indicated, shall be understood to have the following meanings.

An "optical filter system" is in particular a system which includes one optical filter and an objective lens system to receive, pass forward and modify the image light from an object field to an image sensor. The optical filter system is in particular configured to be arranged at a short length in a distal end section of a shaft of the video endoscope.

A "lens system" comprises in particular in an order from an object side a cover glass and/or a first lens, a second lens and/or further lenses, which are arranged along an optical axis of the lens system. In between the first and the second lens of the objective lens system, the optical filter can be located. Preferably the optical filter is positioned at any location within the lens system, where the angle of incidence is significantly far from the perpendicular or where it is suitable due to the kind of lenses. A "lens" in particular is a transmissive optical body that focusses or disperses a light beam (light rays) by means of refraction. The first lens, the second lens, the third and further lenses can be single lenses, which are separated by an air gap or are in contact to adjacent lenses at most pointwise. Also, one lens can be a combined lens or rod lens. Preferably the lenses and/or the cover glass are not cemented to each other. However, in a design of single lenses, these single lenses can be mounted by a functional rim around the respective lenses together. Preferably, the lenses are made of glass and/or a crystalline material. At least one lens has a refractive index n approximately equal to or exceeding 1.6, preferably exceeding 1.7 or even 1.8. At least one lens has an Abbe number v exceeding 70, preferably exceeding 80. Most preferably, one or all lenses of the objective lens system are aspherical and/or some or all optical surfaces of the lenses are aspherical. The aspherical surface maybe convex, concave, and/or may comprise convex, concave and/or plane portion. Preferably, the aspherical surfaces are rotationally symmetric and the axis of symmetry of the lenses are aligned with each other and/or with the optical axis of the objective lens system.

The first lens is preferably a front lens with a high refraction of the steep rays coming from the object field. By the refraction, the front lens preferably decreases the angle of incidence.

The third or the last lens before the image sensor has preferably a negative optical power to direct the image light on the image sensor and/or to adapt the rays to a high chief ray angle of the image sensor.

A "video endoscope" (also denominated simply as "endoscope") is an endoscope with a digital image acquisition and transmission into the proximal end of the video endoscope. The video endoscope comprises an elongate shaft and a handle which are connectable to each other. At least one digital image sensor is located at the distal end (and therewith the side in a distance from the user of the video endoscope) of the elongate shaft for image acquisition. In particular, the video endoscope is any kind of digital endoscope, for example a 2D colonoscope or gastroenteroscope or a 3D video endoscope with, for example, two separated fluorescence objectives. The video endoscope is in particular a chip-on-the-tip (COTT) endoscope, wherein the image sensor as one chip is arranged in the distal end section of the shaft of the video endoscope and the image data collected by the image sensor are transmitted electronically through the shaft towards the proximal side and further to a display system and/or an image processing unit to display the endoscopic image for the user. In particular, in such COTT endoscopes, the objective lens system is employed having a long extension in an axial direction to achieve a near telecentric path. However, the available space in the distal end section of the shaft is limited and therefore a short optical filter system and/or a short objective lens system is used in front of the image sensor. Furthermore, space requirements in the distal end section of the shaft are further limited by additional components, such as illumination light guides, optics and instrument channels in addition to the optical filter system. The video endoscope can be reusable and autoclavable, especially as a medical video endoscope.

The "elongate shaft" is in particular a rigid, semi-flexible or flexible tube. In particular, the shaft is configured for being inserted into a cavity to be viewed endoscopically, for example a body cavity of a human or animal body or another opening in industrial applications, for example a pipe. Generally, the shaft may have an outer diameter in the range of 4 mm to 10 mm. Besides the optical filter system and one or two image sensors, the shaft may comprise one or more channels for irrigation or passing through working instruments (generally referred to as "working channels") in order to achieve the desired effect in the cavity or opening. The shaft can be connected at its proximal end to a handle of a video endoscope or be permanently connected to a handle. Therefore, the shaft may be separately disposable including the optical filter system, the objective lens system and/or the image sensor.

An "electronic image sensor" has in particular its sensor plane in an image plane of the optical filter system and/or objective lens system. The electronic image sensor may be, for example, a charge-coupled device (CCD) or a complementary metal-oxide semiconductor (CMOS). Preferably, the electronic image sensor is a high-definition (HD) image sensor having, for example, full HD resolution. In general, the electronic image sensor is configured to convert the captured image into an electrical image signal and therefore image data. In particular, the electronic image sensor is arranged in the distal end section and/or tip of the shaft and transmits the electrical image signals from the distal end of the shaft to its proximal end by electric transmission lines, such as wires, cables and/or a flexible printed circuit board. Preferably from the shaft the electric image signals generated by the electronic image sensor are transferred further to the handle of the endoscope and/or a display system and/or a processing unit for displaying the captured images. The electronic image sensor can be a mass-produced high-resolution image sensor, for example as used in mobile phones, which includes a micro-lens array with a relatively steep chief ray angle (CRA) wherein the chief ray angle in particular is varying with increasing distance from an optical axis of the objective of the video endoscope. In particular, the micro-lens array arranged on a distal side of the electronic image sensor may have a non-linear CRA function and the optical filter system and/or the objective lens system is adapted to the respective CRA function of the electronic image sensor for correction of chromatic aberration, distortion, shading and/or other aberration. The electronic image sensor has in particular a high CRA with an angle of incidence (AO') of >20°, preferable >30°.

The "at least one successive lens" is in particular a lens with a negative optical power and arranged between the objective lens system and the image sensor. For directing the image light (light rays) on the image sensor, the successive lens is preferably arranged directly in front of the electronic image sensor. The negative optical power of the successive lens serves to modify the chief ray angle characteristics of the optical filter system and/or the objective lens system to the chief ray angle given and required by the electronic image sensor and its micro-lens array. A lens with a negative optical power is in particular called a negative or diverging lens, which spreads a collimated beam of light passing through this lens. A lens with a negative optical power has, for example, biconcave or plano-concave sides or surfaces.

An "optical filter" is in particular a device which selects the incident radiation and/or rays based on specific criteria, such as the wavelength, the polarization state and/or the incident angle or direction. The optical filter is particularly used as an observation and/or detection filter within the optical system. The optical filter can be, for example, a gradient filter with a continuously or discontinuously changing filter effect over the filter surface from the central region to the peripheral region or can be an edge filter with two or more spectral ranges distinctly sharply separated from each other in which the edge filter transmits (and therefore is transparent) or absorbs (and therefore is nontransparent). An edge filter is also a long pass filter (cut-off filter). The optical filter can also be an interference filter or dichroic filter, which is an optical filter that reflects one or more spectral beams or lines and transmits others while maintaining an almost zero coefficient of absorption for all wavelengths of interest. An interference filter comprises in particular multiple thin layer of dielectric material having different refractive indices. The interference filter is in particular wavelength-selective due to the interference effect that occurs between the incident and the reflected waves at the thin layer boundaries. The interference filter comprises in particular a coating which effects a blocking or transmission of the respective light. Preferably, the interference filter completely blocks the excitation light while it transmits the fluorescence emission light with preferably a longer wavelength. Commonly, the interference filter can only select on one angle of incidence and a specific wavelength. The optical filter comprises glass and/or a crystalline material.

Preferably, the optical filter is circular from its center (central point) to its peripheral rim. On the object side and therewith towards the first lens as well as on the opposing side towards the second lens and therewith the image sensor, the optical filter is planar. In the view direction along the optical axis, the optical filter can have a round, rectangular or squared cross section for the light to pass through and/or any other form. Preferably, the center (or center point) of the optical filter falls together with the optical axis. The central region is the region around the center point of the optical filter.

The "optical axis" is in particular a line along which some degree of rotational symmetry exists in an optical system. The optical axis in particular in an imaginary line that defines the path along which light propagates through the optical filter system and the objective lens system towards the electronic image sensor. Preferably, the optical axis passes through the center of curvature of each lens, the optical filter and/or the successive lens. However, the optical axis can also be bent and/or directed by the lenses and/or the optical filter.

"Fluorescence" is in particular an emission of light by a substance (fluorophore) that has absorbed light or other electromagnetic radiation. In particular, the fluorophore is irradiated with a specific excitation wavelength or wavelength band to emit light with a specific emission wavelength or wavelength band. Normally, the emission wavelength or light is longer than the excitation wavelength or light. For excitation, for example, light in the UV region of spectrum is used, while the emission radiation is in the longer wavelength band and therefore in the visible region having lower energy. Depending on the fluorophore, the emission radiation can be seen as a distinctive color. For fluorescence imaging, biological material, such as a tissue for finding a tumor in a body cavity or a bacterium in the environment, is dyed with a fluorophore directly or by administered a substance which is converted into the fluorophore by the body or microorganism before using the video endoscope. By an illumination source and/or filter, an excitation wavelength range is irradiated, for example by an optical fiber, at the distal tip of the shaft on the fluorophore and the emission wavelength range of the fluorophore emitted by the tissue with the tumor is captured by the optical filter system including the objective lens system and the optical filter and transmitted to the image sensor. A "fluorophore" can, for example, be indocyanine green, which absorbs light as well as emits fluorescence in the near infrared range. The excitation wavelength range of indocyanine green is between 600 nm and 900 nm and the emission wavelength range between 750 nm and 950 nm. Other possible fluorophores include protoporphyrin IX (PPIX) with an excitation wavelength range around 405 nm and an emission wavelength range of around 620 nm to 700 nm, and fluorescein with a maximum excitation wavelength of 488 nm and an emitted fluorescence in the green spectral range from 500 nm to 600 nm. Additionally, two fluorophores can be used together and therefore dual fluorescence imaging is possible. For this, a 3D video endoscope comprises two separate fluorescence objectives and therefore two optical filter systems as described above, allowing photodynamic diagnostics and imaging. In general, fluorophores can be used, and fluorescence imaging can be conducted with a fluorescence emission preferably outside of the typical visible range of approximately 450 nm to 650 nm. Certainly, also auto fluorescence of a tissue or an environment can be measured without previous colorization by a fluorophore or dye.

By "overlayable" it is meant that fluorescence image data and visible light image data can be observed simultaneously and/or in the same area and consequently displayed together.

In another embodiment of the invention, the optical filter comprises at least two distinct transmission zones forming the varying transmission characteristics, so that at least a dichroic optical filter is formed.

By this, two distinctly separated transmission zones with different transmission characteristics, especially with different wavelength ranges and/or angles of incidence to the filter surface, are provided, which are collected by the electronic image sensor and consequently are observable by the user of the endoscope and/or displayable on a display system. Hereby, the locally separated transmission zones are arranged spaced radially from the center to the peripheral rim of the optical filter.

In order to achieve two or more spectral ranges separated from each other in which the optical filter either transmits or absorbs the light, the optical filter comprises one filter edge, two filter edges, three filter edges and/or further filter edges.

By arranging one filter edge or more filter edges in dependence on the distance from the central region of the filter surface to its peripheral rim, besides the transmission properties, also the area of each transmission zone can be defined by the respective distance between two adjacent filter edges.

A "filter edge" is in particular the filter specific wavelength which divides the absorption (or reflection) and transmission ranges from each other. Arranged radially on the filter surface, one filter edge gives in particular two different transmission zones on both sides of the filter edge at the surface of the optical filter.

Two or more filter edges can each have the same distance to the adjacent filter edge or, preferably, the filter edges each have different distances between each other in the direction from the central region to the peripheral region of the optical filter and therewith defining different transmission zones.

In a further embodiment of the optical filter system, the optical filter comprises a transmission gradient from the central region to a peripheral region of the optical filter forming the varying transmission characteristics.

Due to the transmission gradient from the central region to the peripheral region, a continuing and/or angular alteration of the transmission characteristics can be achieved. In this case, no abrupt change of the transmission properties over the surface of the optical filter occurs, and therefore distortion and other aberrations can be prevented.

For specifically designing the transmission property from the inner central region to the outer rim of the optical filter, the transmission gradient is designed with a linear and/or non-linear progression from the central region to the peripheral region of the optical filter.

By linear progression of the transmission gradient a continuously rising filter edge shift can be achieved, for example in the longer wavelength direction.

In yet another embodiment of the optical filter system, the transmission characteristics and/or the transmission gradient of the optical filter are adapted to a chief ray angle of the incident image light to the optical filter.

By adapting the transmission characteristics and/or the transmission gradient to the chief ray angle likewise a reliable imaging, especially fluorescence imaging, in requested areas of the image is possible. It is especially advantageous that the transmission gradient changes with a non-linear progression from the central region to the peripheral region of the optical filter whereby each respective filter edge is altered specifically in respect to the changing chief ray angle from the central region of the optical filter to its peripheral region. In case of a round optical filter, the chief ray angle (CRA) as well as the wavelength A of each respective filter edge change varies outwardly with the radius.

The "chief ray angle (CRA)" of the image light, which incidents to the optical filter, is in particular the respective angle of the rays varying with increasing distance from the central region and/or the optical axis of the optical filter system, the objective lens system and/or the optical filter itself. The chief ray angle of the incident light to the optical filter shall not be confused with the chief ray angle of the micro-lenses of the electronic image sensor, as described above for a mass-produced image sensor. Therefore, an adaption of the changing angle of incidence (AO') in a distance from the central region of the optical filter is enabled, in particular the radial changing AOI. Furthermore, it can be complied with the angular spreading of the rays in the optical filter system resulting from the high CRA required by the micro-lenses of the electronic image sensor by adapting the transmission characteristics and/or the transmission gradient of the optical filter to the chief ray angle. Therefore, the optical filter is a connection link in adaption of the CRA progression of the optical filter system to this required CRA progression of the electronic image sensor.

In another embodiment of the invention, the optical filter is designed as a multi-region interference filter.

Therewith, by multiple zones in fluorescence imaging, different single excitation wavelength bands can be reflected or absorbed selectively, while different emission wavelength bands are maintained and transmitted to the optical filter.

For the optimal adaption of the incident rays to the optical filter and its arrangement between the first lens and the second lens, the optical filter is circular and/or planar.

Due to a circular form and therewith a radially symmetric distance from the center to the peripheral region, the transmission characteristics and/or transmission gradient can be easily made dependent on the radius of the optical filter. As the optical filter has one or preferably two planar sides, the optical filter can be located and/or mounted directly on a rim of the aspherical or spherical side of the first lens and/or the second lens without any necessary adaption to the form of the respective lens side.

For focusing the light rays coming from the object field towards the optical axis of the optical filter system, at least one lens of the objective lens system has a positive refractive power.

Preferably, the first lens of the objective lens system has the positive refracting power and therewith enables a short optical system.

A lens with a "positive refractive power" is in particular a lens which converges and/or focusses the light rays. For this, the positive lens comprises, for example, a convex surface. Ideally, a positive lens focusses a collimated beam traveling along the longitudinal axis and therefore along the optical axis to a spot (also called focal point) at a distance from this lens. However, in a short optical system of an endoscope, the rays may not converge into a focal point and are only directed closer to each other.

In a further embodiment, the objective lens system comprises at most three lenses.

By this limited number of lenses in the objective lens system and therewith in the optical filter system, a short optical arrangement for a chip-on-the-tip video endoscope can be provided.

For directing the steep rays from the object field into the optical filter system, the first lens of the objective lens system is a plano-concave lens or a cover glass with a concave depression with a concave side facing towards the image sensor.

Due to the decrease of the angle of incidence coming from the object field by the first lens as a front lens, the chief ray angle becomes closer to the optical axis and the transmission selectivity of the optical filter, in particular an interference filter, becomes more effective.

In another embodiment of the optical filter system, the optical filter is mounted directly on the concave side of the first lens.

By this, a space saving arrangement and a short optical filter system is achieved in which, by arranging the optical filter directly to the concave side of the first lens, no additional air gap exists. Furthermore, in this position of the optical filter, the narrowing of the angle of incidence by the first lens is directly advantageously provided for the required, rather low angle of incidence by the optical filter for blocking and transmitting of specific angles of incidence and/or specific wavelengths.

In a further aspect of the invention, the problem is solved by a display system with a display for displaying images of a video endoscope, wherein the display system is arranged to modify received image data from the video endoscope by a delimiting means adapted to a varying transmission characteristics of an optical filter as described above and/or to a chief ray angle of an image light incident on the optical filter such, that in a central region of the display fluorescence image data and/or an overlay of fluorescence image data and visible light image data and/or in peripheral region visible light data are displayed.

Therewith, a display system is provided with a special display of the image information independent from the transmission characteristics of the optical filter and/or the chief ray angle of an image light incident on the optical filter for the user of the video endoscope. Depending on the sharpness of the filter edges and/or the progression of the transmission characteristics, a direct display of the image data would result in confusing information seen by the user and in an unattractive, indistinct and undefined border region between the two or more transmission zones. Consequently, a suitable imaging and display independent from the filter edges of the observation filter and the illumination filter as well as from the chief ray angle of the observation filter (optical filter) is possible.

This allows in particular displaying also in optical systems which have to place the optical filter, despite the known restriction, at a position in the optical system at which the chief ray angle is increased towards the peripheral region of the optical filter and/or lenses and in which a fluorescence image display is normally not possible in distinct areas. Therefore, by the delimiting means, the display system is suitable for endoscopes with short optical systems. Furthermore, a display of image data is enabled by the display system for optical systems which use an optical filter with one or more filter edges.

In case of a short optical system, the display system is arranged such that only a partial area of the whole field of view is used for fluorescence imaging and the remaining part of the field of view is only used for visible light (white light) imaging. Hereby, the change over from fluorescence imaging to white light imaging occurs in a distance R from the center of the image on the image sensor. The distance R corresponds to the distance for which the following shift applies:

$$\lambda_{i1}-(\lambda_{i1}-\lambda_{ex})+x<\lambda_\theta \quad (I)$$

wherein for $\lambda_\theta$ the following applies:

$$\lambda_\theta = \lambda_o \sqrt{1 - \left(\frac{no}{neff}\sin\theta\right)^2} \quad (II)$$

with
$\lambda_\theta$=wavelength corresponding to the feature of interest at incident angle $\theta$
$\lambda_o$=wavelength corresponding to the feature of interest at normal incidence
$n_o$=refractive index of incident medium
$n_{\mathit{eff}}$=effective refractive index of the optical filter
$\theta$=angle of incidence,
and wherein $\lambda_o$ in the equation (II) exactly correspondents to the filter edge of the fluorescence detection filter $\lambda_{ex}$ and $\lambda_{i1}$ corresponds to the edge of the fluorescence illumination filter. For example, in case of indocyanine green (ICG), $\lambda_{ex}$ is in the range of 810 nm and the edge of the ICG illumination filter $\lambda_{i1}$ is at 795 nm. Hereby, it is assumed that the edge position gives the wavelength at which the transmission has decreased down to 50% (ICG illumination filter) or increased up to 50% (ICG detection filter). In equation (I), x determines the minimal distance of the filter edge of the observation filter from the illumination filter, for which a distinct fluorescence displaying can be assured. This depends on the steepness of the edge and, in general, can be given as:

$$1\ nm<x<100\ nm \quad (III)$$

Overall, the distance and/or radius R of the fluorescence image depends on the filter characteristics of the illumination and detection filter as well as on the angle of incidence $\theta$, measured towards the perpendicular, of the main rays for the different fields of view for the filter.

In case the optical filter is designed as an interference filter with distinct transmission zones, the display system clearly defines the distinct view regions. For example, in case of a dual region interference filter, a central area displays fluorescence and/or white light data in a first distance or radius R1. In an area from the radius R1 to a greater radius R2 from the center of the image, reliable fluorescence data is displayed, and in the outer remaining area, the displayed image only shows reliable visible light data. By the distinct displaying in specific areas, the user of the video endoscope gets reliable and clear information.

A "delimiting means" is in particular a tool by which the received image data are modified for displaying. The delimitating means is in particular implemented by software and/or algorithm. Hereby, known digital image processing methods can be applied, such as histogram equalization, pixel connectivity, global operations and/or filtering.

In a further embodiment of the display system, the delimiting means is adapted to the optical filter such, that a largest amount of visible image data and fluorescence image data are displayed in the central region, in a middle region reliable fluorescence image data and less visible light image data and in the peripheral region visible light image data are displayed.

Hereby, the less visible light data in the middle region is caused by the shift of the filter edge of the optical filter.

For marking the different regions, the display system comprises a visible indicator, a color indicator, a frame indicator and/or a text indicator.

Therewith, the different regions can be differentiated for example by a slight shadowing in the transition from one area to the next and/or by different adaption of the coloring. Furthermore, different coloring can be achieved via a blue channel or by the color saturation. In general, any coloring can be used for displaying the fluorescence. In addition to using colors or instead of using colors, also grey shades can be shown. Furthermore, grey shades can be overlaid with colored masks to demonstrate to the user of the video endoscope that in certain areas another or no reliable fluorescence display of the system exists.

Furthermore, a distinct frame around each area in black or a specific color is possible by the frame indicator. Also, by text indicators, text can be shown in the respective area to give an indication whether it is the visible light or fluorescence zone.

Generally, it has to be stressed that the displayed image can have any form and/or aspect ratio. Preferably, the displayed image is circular and, preferably, also the filter is circular. However, the image and/or the optical filter can also have an oval form.

In another embodiment, the display system comprises a mask for indicating an area with unsure image data display.

Consequently, the user of the display system and the associated video endoscope gets a clear indication as to in which area reliable and unreliable image data is displayed, and therefore, at first view, the user can see which displayed data can be used for further decisions and handling.

For marking areas with unsure image data, the mask, for example, can show a unique overlay, blur or smoothing by a Gaussian filter or changes by gradient filter can be applied.

In another aspect of the invention, the problem is solved by a video endoscope, in particular medical or industrial video endoscope, with a handle, an elongate shaft and a light source, wherein the video endoscope comprises an optical filter system as described above, so that in case of fluorescence imaging an emission radiation is collectable by the image sensor free from contamination from excitation radiation and/or fluorescence image data and/or a visible light image are overlayable and/or displayable.

Consequently, a video endoscope is provided, such as colonoscope or gastroscope, with a reliable 2D or 3D white light, fluorescence and/or overlaid imaging. Therewith, a photodynamic diagnostic is enabled in medical application of the video endoscope as well as the detection, for example of different bacteria, in industrial applications of the video endoscope.

In a further embodiment of the video endoscope, the video endoscope comprises a display system as described above.

Therewith, one, two or more further fluorophores or other dyes can be respectively imaged by the display system of the video endoscope.

Instead of a video endoscope, certainly the optical filter system and/or the display system can also be used in a camera.

The invention is further explained by the following exemplary description of particular embodiments, and the figures.

DETAILED DESCRIPTION OF THE INVENTION

A video endoscope 101 comprises a handle 103 and an elongate shaft 105 connectable to each other at a proximal end 107 of the shaft 105. The handle 103 comprises operator controls 115 and is connected via a cable 113 at its proximal end to an external, non-shown control and processing unit and to a display system 201 shown in FIG. 1. The display system 201 includes a monitor 203 for displaying endoscopic images and operator controls 215.

Figure 1:
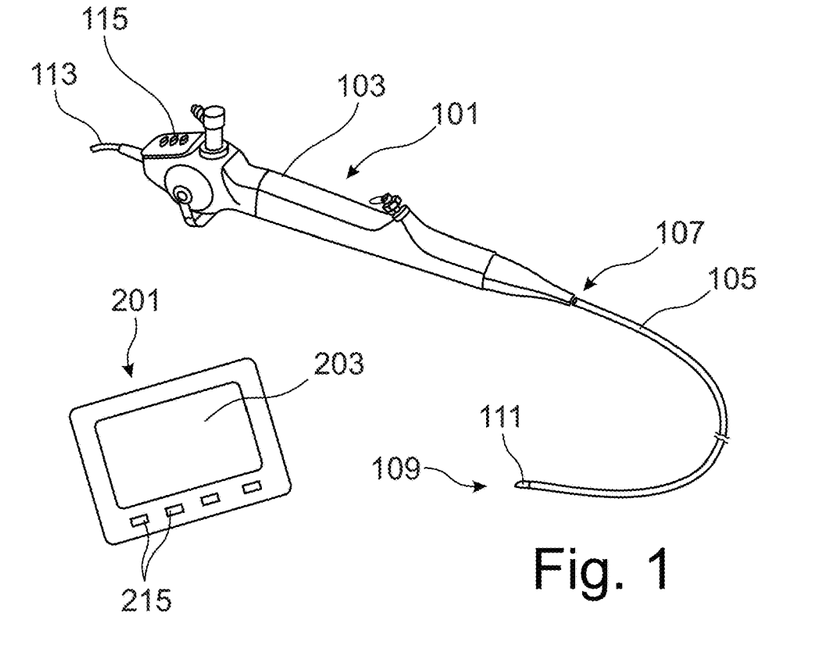
FIG. 1 is a schematic partially three-dimensional view of an endoscope and a display system.

The video endoscope 101 is designed to provide video and image data from an objective field within a cavity of a non-shown body. For this, the elongate shaft 105 comprises at its distal end 109 a distal end section 111.

Figure 2:
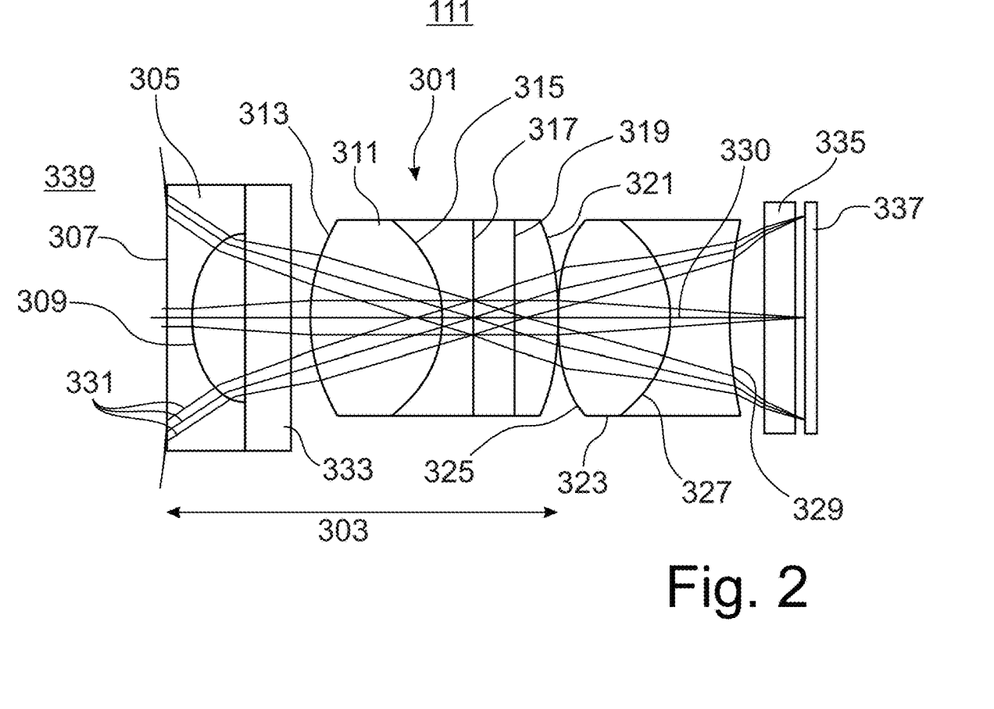
FIG. 2 is a schematic section view of an optical filter system and an image sensor.

The distal end section 111 of the elongate shaft 105 comprises an optical filter system 301 and an image sensor 337 with a cover plate 335. The optical filter system 301 comprises an objective lens system 303 with a first lens 305 and a second lens 311, wherein the first lens is designed as a front lens and the second lens 311 as a combined lens. In the order from an object side 339, a third lens 323 follows after the objective lens system 303.

The first lens 305 has a planar side 307 directed to the object side 339. On the opposite side of the first lens 305, a concave side 309 is arranged. On a rim surrounding this concave side 309, an interference filter 333 is mounted. In direction of an optical axis 330, the interference filter 333 is planar on both sides. The planar side of the interference filter 333 directed towards the image sensor 337 is placed a distance away from a convex side 313 of the second lens 311. The second lens 311 includes a concave surface 315, a planar surface 317, another planar surface 319 and a convex side 321. The convex side 321 is adjacent to an opposite oriented convex side 325 of the third lens 323 designed as a combined lens. The third lens 323 further comprises a concave surface 327 directed to the object side 339 and a concave side 329 directed to the image sensor 337. On the concave side 329, the third lens 323 is spaced by an air gap to the cover plate 335 of the image sensor 337.

The optical filter system 301 with the objective lens system 303 is designed as a short optical system. The planar interference filter 333 is consequently located within the objective lens system 303 in a position between the first lens 305 and the second lens 311, wherein the chief ray angle (CRA) of the light rays 331 incident on the interference filter 333 have a higher angle of incidence at the peripheral region of the interference filter 333 than the light rays 331 incident near a central region of the interference filter 333 and therewith close to the optical axis 330.

By a non-shown light source and a non-shown fiber optical cable of the video endoscope 101, illumination light and excitation light are radiated on an object field within the body cavity. A tissue in the body cavity has previously been colored by indocyanine green (ICG) and consequently a maximum peak of 795 nm is used for excitation. The indocyanine green emits fluorescence light with a maximum peak at 810 nm, so that the maximum excitation wavelength 795 nm and the emission wavelength 820 nm are very close together.

The steep light rays 331 coming from the object field are converged by the concave side 313 of the first lens 305 and are transmitted through the interference filter 333, so that the light rays 331 come closer to and along the optical axis 330 at the planar surface 317 of the second lens 311. Afterwards, by means of the convex side 321 of the second lens 311 and the convex side 325, the concave surface 327 and the concave side 329, the light rays 331 are diverged towards the cover plate 335 in order to meet the requirements of the steep chief ray angle of the non-shown micro-lenses of the image sensor 337, which is designed as a CMOS with a high HD resolution.

Figure 3:
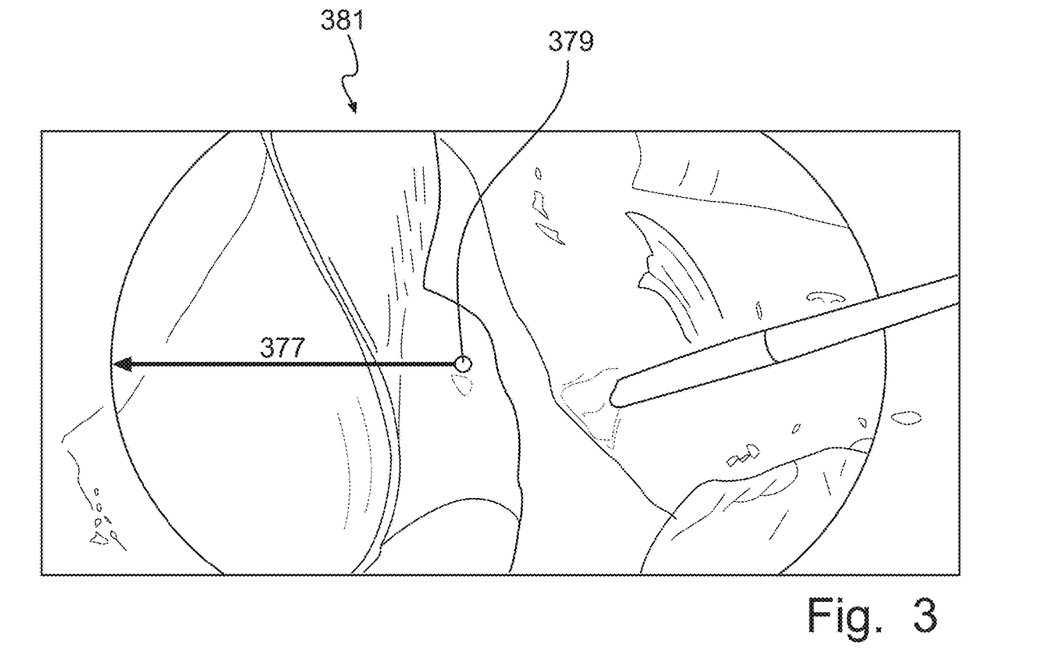
FIG. 3 shows a displayed endoscopic image in black/white.
Figure 5:
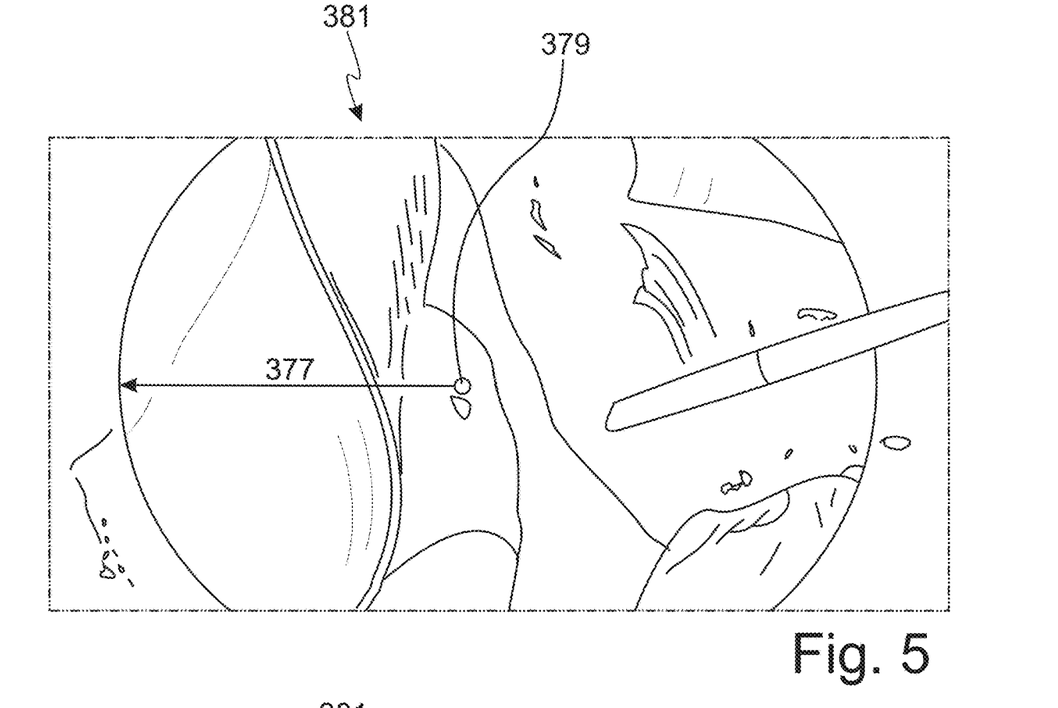
FIG. 5 is an illustration of the displayed endoscopic image of FIG. 3.
Figure 6:
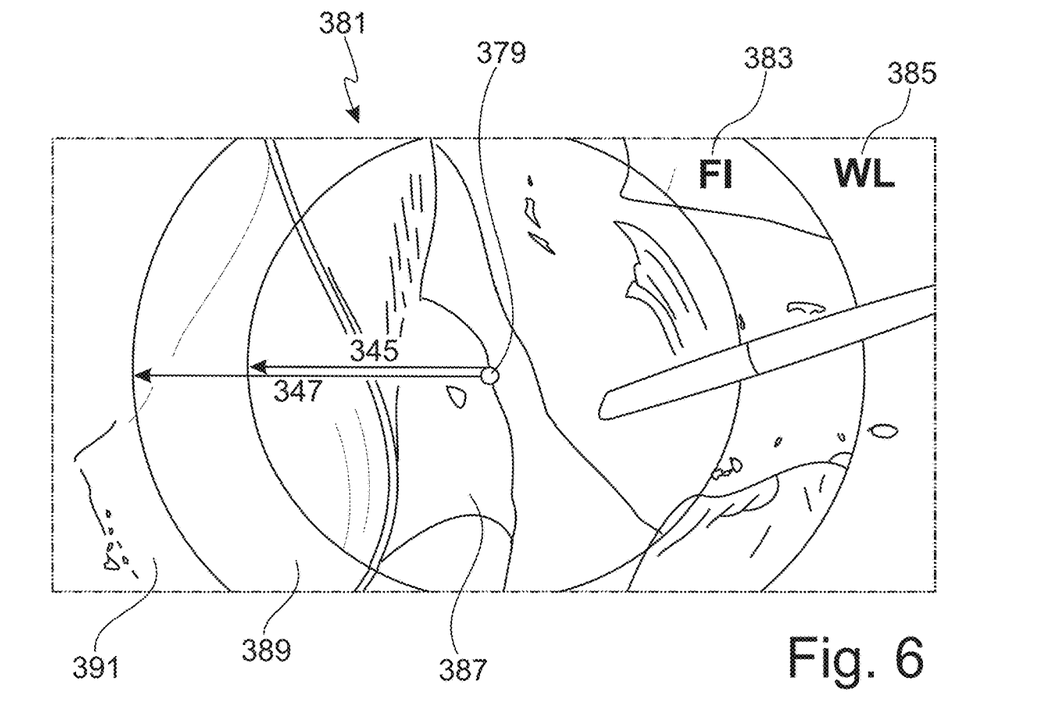
FIG. 6 is an illustration of the displayed endoscopic image of FIG. 4.

An endoscopic image 381 received by the image sensor 337 and modified by the display system 201 is shown in FIG. 3 in black and white and in FIG. 5 as a drawing. In dependence on the transmission characteristics of the interference filter 333 as well as the minimal distance of a filter edge of the non-shown illumination filter of the light source and the interference filter 333 as detection filter and further an edge steepness (as given in equations I to III above), a radius 377 from a central region 379 of the endoscopic image 381 is determined which defines a central area around the central region 379 in which a reliable fluorescence data display and/or overlay of fluorescence image data and white light (visible light) image data is displayed. In the peripheral region outside of the radius 377, only white light data is displayed. While shown in FIG. 3 only in black and white, modified by the display system 201, in reality the reliable fluorescence image data is shown in a green color, wherein the transmission from the inner central region with the reliable fluorescence image data and/or the overlaid visible light is indicated by a gray frame (at the arrowhead of the radius 377) and the peripheral area with the visible light only region is marked with a grey shadow.

Figure 7:
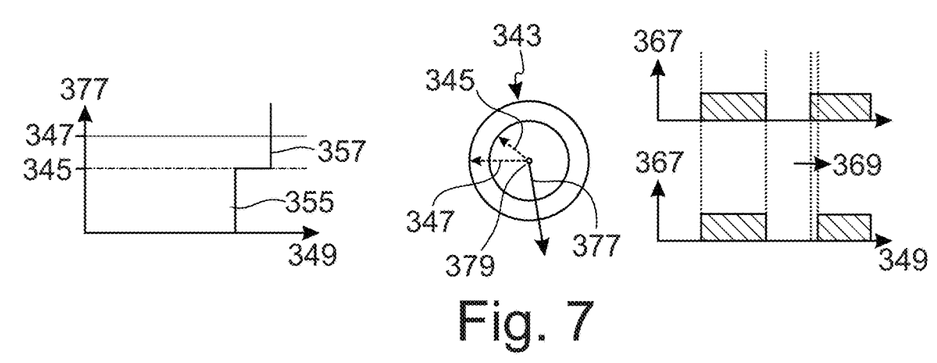
FIG. 7 is a schematic view of a filter surface of a dual region interference filter with a representation showing filter edges in dependence on wavelength and transmission in dependence on wavelength.

In an alternative, the interference filter 333 as shown in FIG. 2 is a dual-region interference filter 343 (FIG. 7). Viewing on the filter surface, the dual-region interference filter 343 comprises from its central region 379 with increasing radius 377 a first transmission zone with a first radius 345 and a peripheral second transmission zone with a second radius 347.

The filter surface of the dual-region interference filter 343 from the central region to the first radius 345 has a first filter edge 355 with a certain wavelength 349, wherein the first filter edge 355 shifts abruptly at the first radius 345 to a second filter edge 357 with a longer wavelength 349. Respectively, in the representation of the transmission 367 in dependence on the wavelength 349 in FIG. 7, a shift of the filter edge 369 occurs from the inner central first transmission zone with the first radius 345 to the peripheral second transmission zone with the second radius 347 of the filter surface of the dual-region interference filter 343. Therefore, reliable fluorescence image data is transmitted in the peripheral area between the first radius 345 and the second radius 347, as the excitation light with a shorter wavelength is blocked here by the dual-region interference filter 343. However, a direct display of the image data from the image sensor 337 would result in confusing information seen by a user on the monitor 203. Therefore, the received image from the image sensor 337 is modified by the display system 201 and explicit regions are defined as shown in the displayed endoscopic image 381 in FIG. 4 in black and white, wherein a central region 387 around the central region 379 with the first radius 345 has the largest amount of visible data and fluorescence data. In a middle region between the first radius 345 and the second radius 347, reliable fluorescence data but generally less visible light data due to the shift of the filter edge 369 are displayed. Further outwards from the second radius 347 in the peripheral region 391, only visible light data is displayed. The central region 387, the middle region 389 and the peripheral region 391 are marked at the respective transitions with a gray frame. Furthermore, the fluorescence image data in the central region 387 as well as the reliable fluorescence data in the middle region 389, which is not influenced by the white light and the excitation light, is given in green color in reality.

Figure 4:
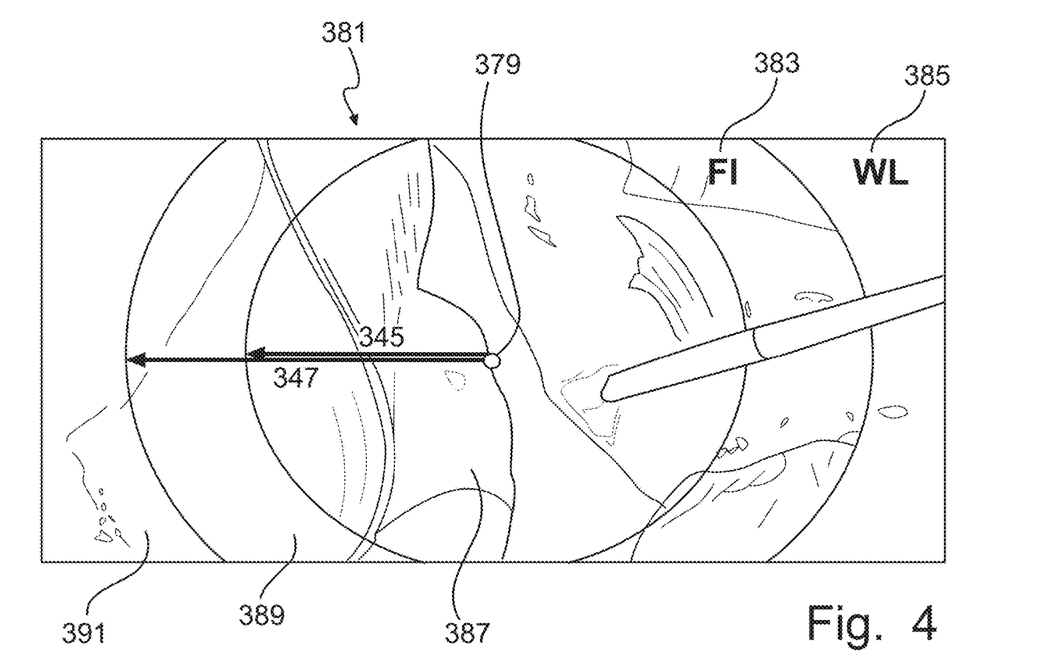
FIG. 4 shows another displayed endoscopic image in black/white.

Furthermore, in the middle region 389, an Fl indicator 383 is given indicating the reliable fluorescence data. Likewise, in the peripheral region 391, a white light indicator 385 giving "WL" is shown.

Consequently, a dual-region interference filter 343 is provided which allows a collection of emission radiation for fluorescence imaging by the image sensor 337 without any interference from an excitation radiation. Furthermore, reliable fluorescence image data and visible light image data are displayable and overlayable in distinct regions.

Figure 8:
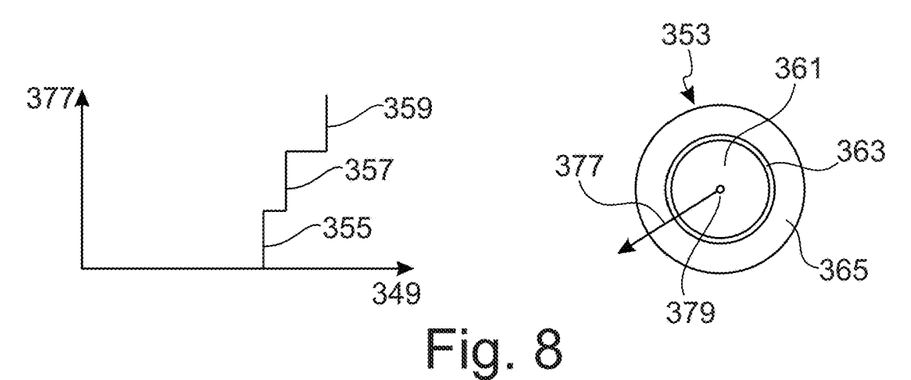
FIG. 8 is a front view of a multi-region interference filter with a representation of filter edges in dependence on wavelength.

In a further alternative, the interference filter 333 is designed as a multi-region interference filter 353 (see FIG. 8). The multi-region interference filter 353 has, from its central region 379, a first transmission zone 361, a second transmission zone 363 and a third transmission zone 365 with increasing radius 377. Consequently, with the increasing radius 377, a first filter edge 355 switched abruptly to a second filter edge 357 with a longer wavelength at the transition between the first transmission zone 361 to the second transmission zone 363. Likewise, at the transition from the second transmission zone 363 to the third transmission zone 365, the second filter edge 357 is changed abruptly to a third filter edge 359. Consequently, a multi-region interference filter 353 with a respective transmission characteristic is provided.

Figure 9:
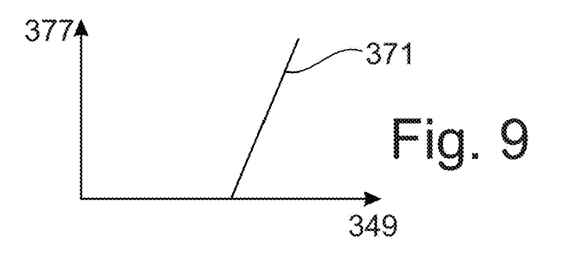
FIG. 9 shows a representation of continuous filter edge gradient in dependence on radius and wavelength.

In a further alternative, the interference filter 333 is designed with a continuous linear filter edge gradient 371, wherein the filter edge is continuously shifted towards a longer wavelength with increasing radius 377.

Figure 10:
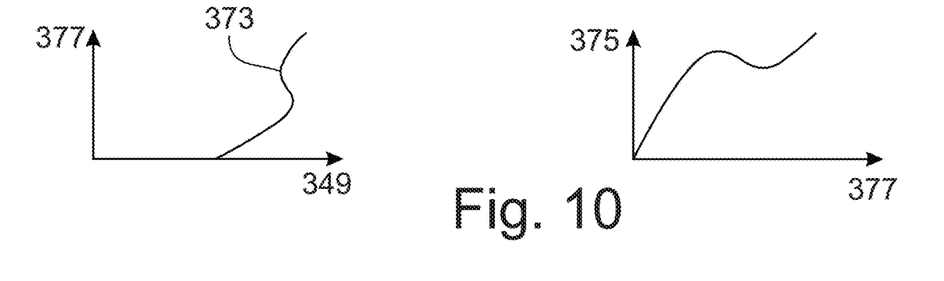
FIG. 10 shows a representation of a non-linear filter edge gradient in dependence on radius and wavelength and a chief ray array at the filter surface in dependence on the radius.

In a further alternative, the interference filter 333 has a non-linear filter edge gradient 373, whereby the progression of the non-linear filter edge gradient 373 with increasing radius 377 and increasing wavelength 349 is adapted to a chief ray angle (CRA) at the filter surface 375, whereby the CRA increases non-linear with increasing radius 377. Consequently, the respective filter edge corresponds to an angle of incidence at the filter surface of the interference filter 333. Therewith, an adaptation of the transmission characteristic of the interference filter 333 to the angular, radially changing angle of incidence is achieved.

REFERENCE NUMERALS 101 video endoscope
103 handle
105 elongate shaft
107 proximal end of shaft
109 distal end of shaft
111 distal end section
113 cable
115 operator controls
201 display system
203 monitor
215 operators controls
301 optical filter system
303 objective lens system
305 first lens
307 planar side
309 concave side
311 second lens (combined lens)
313 convex side
315 concave surface
317 planar surface
319 planar surface
321 convex side
323 third lens (combined lens)
325 convex side
327 concave surface
329 concave side
330 optical axis
331 light rays
333 interference filter
335 cover plate
337 image sensor
339 object side
343 dual region interference filter
345 first radius
347 second radius
349 wavelength λ
353 multi-region interference filter
355 first filter edge
357 second filter edge
359 third filter edge
361 first transmission zone
363 second transmission zone
365 third transmission zone
367 transmission
369 shift of filter edge
371 continuous filter edge gradient
373 non-linear filter edge gradient
375 CRA at filter surface
377 radius
379 central region
381 endoscopic image
383 Fl indicator
385 white light indicator
387 central region
389 middle region
391 peripheral region

The invention claimed is:

1. An optical filter system for inclusion into a distal end section of a video endoscope with an electronic sensor arranged in an image plane in the distal end section for receiving image light, the optical filter system comprises:
    an objective lens system including at least a first lens, a second lens, and a third lens that are arranged in order from an object side to receive the image light and to pass the image light to the image sensor;
    an optical filter optically located between the first lens and the second lens of the objective lens system, the optical filter being planar on both sides, wherein one side is an object side and the other side is an image side, the optical filter including a coating having a variable transmission that varies along a radius originating_ from a center of a_central region of the optical filter to and extending to a peripheral region of the optical filter to transmit a predetermined wavelength of light from the central region to the peripheral region and block excitation light while allowing fluorescence light to pass.

2. The optical filter system of claim 1, wherein the optical filter comprises at least two distinct transmission zones to define a dichroic optical filter.

3. The optical filter system of claim 2, characterized in that the optical filter comprises two or more filter edges.

4. The optical filter system of claim 1, wherein the coating has a transmission gradient from the central region to the peripheral region.

5. The optical filter system of claim 4, wherein the transmission gradient has a non-linear progression from the central region to the peripheral region of the optical filter.

6. The optical filter system of claim 1, wherein the coating is adapted to a chief ray angle of the incident image light to the optical filter.

7. The optical filter system of claim 1, wherein the optical filter is a multi-region interference filter.

8. The optical filter system of claim 1, wherein the optical filter is circular.

9. The optical filter system of claim 1, wherein at least one lens of the objective lens system has a positive refractive power.

10. The optical filter system of claim 1, wherein the objective lens system comprises at most three lenses.

11. The optical filter system of claim 1, wherein the first lens of the objective lens system is a plano-concave lens.

12. The optical filter system of claim 11, wherein the optical filter is mounted directly adjacent to the concave side of the first lens.

13. The optical filter system as set forth in claim 1, wherein an angle of incidence at a peripheral region of the optical filter is higher than an angle of incidence at a central region of the optical filter.

14. A video display system comprising:
    a display, for simultaneously displaying a fluorescence image and a visible light image;

a video endoscope for collecting the fluorescence image and the visible light image, the video endoscope includes:

an image sensor; and an objective lens system including at least a first lens, a second lens, and a third lens in order from an object side to receive an image light and to pass the image light to the image sensor, the image sensor and the objective lens system configured to collect fluorescence image data and visible light image data, the objective lens system includes an optical filtration system, and the optical filtration system includes a filter element optically located between the first lens and the second lens of the objective lens system, the filter element being planar on both sides, wherein one side is an object side and the other side is an image side, the filter element further including a coating having a variable transmission that varies radially from a center of the filter element to a periphery of the filter element; and wherein fluorescence image data and/or an overlay of fluorescence image data and visible light image data are displayed in a central region of the display; visible light data is displayed in a peripheral region of the display; and a delimiting means is displayed between the central region and the peripheral region.

15. The video display system of claim 14, wherein the delimiting means is adapted to the optical filter, such that a largest amount of visible image data and fluorescence image data is displayed in the central region; in a middle, between the central region and the peripheral region, reliable fluorescence image data and less visible light image data than in the central region is displayed; and in the peripheral region only visible light image data displayed.

16. The video display system of claim 15, wherein the display system comprises a visible indicator being a color indicator, a frame indicator, and/or a text indicator for marking the different regions.

17. The video display system of claim 14, wherein the display system comprises a visible indicator being a color indicator, a frame indicator, and/or a text indicator for marking the different regions.

18. The video display system of claim 14, wherein the display system comprises a mask for indicating an area with unreliable fluorescence image data.

19. A video endoscope comprising:

a handle;

an elongate shaft having a distal end section;

an image sensor for receiving image light arranged in an image plane in the distal end section;

and an optical filter system including an objective lens system having at least a first lens, a second lens, and a third lens that are arranged in order from an object side to receive the image light and to pass the image light to the image sensor, wherein the optical filter system includes an optical filter optically located between the first lens and the second lens of the objective lens system, the optical filter being planar on both sides, wherein one side is an object side and the other side is an image side, the optical filter including a coating having a variable transmission that varies along a radius originating from a center of a central region of the optical filter and extending to a peripheral region of the optical filter so as to transmit a predetermined wavelength of light from the central region to the peripheral region and block excitation light while allowing fluorescence light to pass.

20. The video endoscope as set forth in claim 19, wherein an angle of incidence at a peripheral region of the optical filter is higher than an angle of incidence at a central region of the optical filter.

* * * * *